(12) United States Patent
Mustufa et al.

(10) Patent No.: US 11,786,325 B2
(45) Date of Patent: Oct. 17, 2023

(54) REMOTELY CONTROLLING A SYSTEM USING VIDEO

(71) Applicant: Intuitive Surgical Operations, Inc., Sunnyvale, CA (US)

(72) Inventors: Tabish Mustufa, Sunnyvale, CA (US); Brandon Itkowitz, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 229 days.

(21) Appl. No.: 16/904,482

(22) Filed: Jun. 17, 2020

(65) Prior Publication Data

US 2021/0000557 A1  Jan. 7, 2021

Related U.S. Application Data

(60) Provisional application No. 62/869,587, filed on Jul. 2, 2019.

(51) Int. Cl.
*B25J 9/16* (2006.01)
*A61B 34/35* (2016.01)
(Continued)

(52) U.S. Cl.
CPC .............. *A61B 34/35* (2016.02); *A61B 34/20* (2016.02); *A61B 34/25* (2016.02); *A61B 34/37* (2016.02);
(Continued)

(58) Field of Classification Search
CPC ......... A61B 34/35; A61B 34/20; A61B 34/25; A61B 34/37; A61B 2034/2074; A61B 2090/372; A61B 90/361; A61B 18/12; A61B 2090/371; B25J 9/1689; B25J 9/1697; B25J 13/06; B25J 13/08;
(Continued)

(56) References Cited

U.S. PATENT DOCUMENTS 4,305,539 A  12/1981 Korolkov et al.
4,319,576 A  3/1982 Rothfuss
(Continued)

FOREIGN PATENT DOCUMENTS

EP  0277532 B1  8/1990
EP  0277529 B1  4/1993
(Continued)

OTHER PUBLICATIONS

International Search Report and Written Opinion for Application No. PCT/US2020/054568, dated Jan. 29, 2021, 13 pages.
(Continued)

*Primary Examiner* — Bao Long T Nguyen
(74) *Attorney, Agent, or Firm* — Farber LLC (57) ABSTRACT

Systems and methods for remotely controlling a system using video are provided. A method in accordance the present disclosure includes detecting a video signal of an auxiliary system at a video input, wherein the video signal including images encoded with control information. The method also includes determining that the images included in the video signal include the control information. The method further includes extracting the control information from the images. Additionally, the method includes modifying operations of the system based on the control information.

16 Claims, 5 Drawing Sheets

(51) Int. Cl.
*A61B 34/00* (2016.01)
*A61B 34/37* (2016.01)
*G06T 7/20* (2017.01)
*G06T 13/20* (2011.01)
*A61B 34/20* (2016.01)

(52) U.S. Cl.
CPC .............. *B25J 9/1689* (2013.01); *G06T 7/20* (2013.01); *G06T 13/20* (2013.01); *A61B 2034/2074* (2016.02)

(58) Field of Classification Search
CPC ........... B25J 19/023; B25J 19/04; G06T 7/20; G06T 13/20; G05B 2219/40174; G05B 2219/40413; G05B 2219/40002; G05B 2219/40005; G06F 3/005; G06F 3/01–013; G06F 3/017
See application file for complete search history.

(56) References Cited

U.S. PATENT DOCUMENTS

| | | |
|---|---|---|
| 4,407,286 A | 10/1983 | Noiles et al. |
| 4,429,695 A | 2/1984 | Green |
| 4,509,518 A | 4/1985 | McGarry et al. |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,767,044 A | 8/1988 | Green |
| 4,809,695 A | 3/1989 | Gwathmey et al. |
| 4,848,637 A | 7/1989 | Pruitt |
| 4,892,244 A | 1/1990 | Fox et al. |
| 4,930,503 A | 6/1990 | Pruitt |
| 4,978,049 A | 12/1990 | Green |
| 5,027,834 A | 7/1991 | Pruitt |
| 5,040,715 A | 8/1991 | Green et al. |
| 5,133,735 A | 7/1992 | Slater et al. |
| 5,133,736 A | 7/1992 | Bales, Jr. et al. |
| 5,147,357 A | 9/1992 | Rose et al. |
| 5,180,092 A | 1/1993 | Crainich |
| 5,275,323 A | 1/1994 | Schulze et al. |
| 5,307,976 A | 5/1994 | Olson et al. |
| 5,312,023 A | 5/1994 | Green et al. |
| 5,334,183 A | 8/1994 | Wuchinich |
| 5,342,395 A | 8/1994 | Jarrett et al. |
| 5,342,396 A | 8/1994 | Cook |
| 5,366,133 A | 11/1994 | Geiste |
| 5,452,836 A | 9/1995 | Huitema et al. |
| 5,452,837 A | 9/1995 | Williamson, IV et al. |
| 5,480,089 A | 1/1996 | Blewett |
| 5,484,095 A | 1/1996 | Green et al. |
| 5,484,451 A | 1/1996 | Akopov et al. |
| 5,487,500 A | 1/1996 | Knodel et al. |
| 5,497,931 A | 3/1996 | Nakamura |
| 5,533,521 A | 7/1996 | Granger |
| 5,540,375 A | 7/1996 | Bolanos et al. |
| 5,554,164 A | 9/1996 | Wilson et al. |
| 5,560,530 A | 10/1996 | Bolanos et al. |
| 5,562,239 A | 10/1996 | Boiarski et al. |
| 5,564,615 A | 10/1996 | Bishop et al. |
| 5,571,116 A | 11/1996 | Bolanos et al. |
| 5,571,285 A | 11/1996 | Chow et al. |
| 5,573,534 A | 11/1996 | Stone |
| 5,615,820 A | 4/1997 | Viola |
| 5,624,452 A | 4/1997 | Yates |
| 5,628,446 A | 5/1997 | Geiste et al. |
| 5,651,491 A | 7/1997 | Heaton et al. |
| 5,652,849 A * | 7/1997 | Conway ................. G08B 25/14 701/25 |
| 5,667,626 A | 9/1997 | Cayford et al. |
| 5,673,842 A | 10/1997 | Bittner et al. |
| 5,676,674 A | 10/1997 | Bolanos et al. |
| 5,688,269 A | 11/1997 | Newton et al. |
| 5,690,269 A | 11/1997 | Bolanos et al. |
| 5,693,042 A | 12/1997 | Boiarski et al. |
| 5,697,542 A | 12/1997 | Knodel et al. |
| 5,700,270 A | 12/1997 | Peyser et al. |
| 5,700,276 A | 12/1997 | Benecke |
| 5,709,680 A | 1/1998 | Yates et al. |
| 5,752,644 A | 5/1998 | Bolanos et al. |
| 5,752,973 A | 5/1998 | Kieturakis et al. |
| 5,762,255 A | 6/1998 | Chrisman et al. |
| 5,762,256 A | 6/1998 | Mastri et al. |
| 5,779,130 A | 7/1998 | Alesi et al. |
| 5,782,396 A | 7/1998 | Mastri et al. |
| 5,792,135 A | 8/1998 | Madhani et al. |
| 5,820,009 A | 10/1998 | Melling et al. |
| 5,826,776 A | 10/1998 | Schulze et al. |
| 5,833,695 A | 11/1998 | Yoon |
| 5,865,361 A | 2/1999 | Milliman et al. |
| 5,871,135 A | 2/1999 | Williamson, IV et al. |
| 5,911,353 A | 6/1999 | Bolanos et al. |
| 5,915,616 A | 6/1999 | Viola et al. |
| 5,941,442 A | 8/1999 | Geiste et al. |
| 5,954,259 A | 9/1999 | Viola et al. |
| 5,959,892 A | 9/1999 | Lin et al. |
| 6,032,849 A | 3/2000 | Mastri et al. |
| 6,079,606 A | 6/2000 | Milliman et al. |
| 6,174,309 B1 | 1/2001 | Wrublewski et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,330,956 B1 | 12/2001 | Willinger |
| 6,330,965 B1 | 12/2001 | Milliman et al. |
| 6,488,196 B1 | 12/2002 | Fenton, Jr. |
| 6,503,259 B2 | 1/2003 | Huxel et al. |
| 6,585,735 B1 | 7/2003 | Frazier et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,786,382 B1 | 9/2004 | Hoffman |
| 6,817,974 B2 | 11/2004 | Cooper et al. |
| 6,877,647 B2 | 4/2005 | Green et al. |
| 6,905,057 B2 | 6/2005 | Swayze et al. |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,986,451 B1 | 1/2006 | Mastri et al. |
| 6,988,649 B2 | 1/2006 | Shelton, IV et al. |
| 7,000,818 B2 | 2/2006 | Shelton, IV et al. |
| 7,000,819 B2 | 2/2006 | Swayze et al. |
| 7,044,352 B2 | 5/2006 | Shelton, IV et al. |
| 7,044,353 B2 | 5/2006 | Mastri et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,114,642 B2 | 10/2006 | Whitman |
| 7,128,253 B2 | 10/2006 | Mastri et al. |
| 7,140,527 B2 | 11/2006 | Ehrenfels et al. |
| 7,140,528 B2 | 11/2006 | Shelton, IV et al. |
| 7,258,262 B2 | 8/2007 | Mastri et al. |
| 7,308,998 B2 | 12/2007 | Mastri et al. |
| 7,328,828 B2 | 2/2008 | Ortiz et al. |
| 7,380,695 B2 | 6/2008 | Doll et al. |
| 7,380,696 B2 | 6/2008 | Shelton, IV et al. |
| 7,398,908 B2 | 7/2008 | Holsten et al. |
| 7,401,721 B2 | 7/2008 | Holsten et al. |
| 7,407,075 B2 | 8/2008 | Holsten et al. |
| 7,455,676 B2 | 11/2008 | Holsten et al. |
| 7,472,814 B2 | 1/2009 | Mastri et al. |
| 7,481,349 B2 | 1/2009 | Holsten et al. |
| 7,494,039 B2 | 2/2009 | Racenet et al. |
| 7,565,993 B2 | 7/2009 | Milliman et al. |
| 7,588,174 B2 | 9/2009 | Holsten et al. |
| 7,654,431 B2 | 2/2010 | Hueil et al. |
| 7,673,783 B2 | 3/2010 | Morgan et al. |
| 7,699,835 B2 | 4/2010 | Lee et al. |
| 7,721,930 B2 | 5/2010 | McKenna et al. |
| 7,726,539 B2 | 6/2010 | Holsten et al. |
| 7,770,774 B2 | 8/2010 | Mastri et al. |
| 7,794,475 B2 | 9/2010 | Hess et al. |
| 7,832,611 B2 | 11/2010 | Boyden et al. |

(56) References Cited

U.S. PATENT DOCUMENTS

| | | |
|---|---|---|
| 7,837,079 B2 | 11/2010 | Holsten et al. |
| 7,866,526 B2 | 1/2011 | Green et al. |
| 7,942,303 B2 | 5/2011 | Shah et al. |
| 7,950,561 B2 | 5/2011 | Aranyi |
| 8,070,035 B2 | 12/2011 | Holsten et al. |
| 8,083,118 B2 | 12/2011 | Milliman et al. |
| 8,127,975 B2 | 3/2012 | Olson et al. |
| 8,157,152 B2 | 4/2012 | Holsten et al. |
| 8,272,553 B2 | 9/2012 | Mastri et al. |
| 8,308,042 B2 | 11/2012 | Aranyi |
| 8,348,127 B2 | 1/2013 | Marczyk |
| 8,365,972 B2 | 2/2013 | Aranyi et al. |
| 8,371,492 B2 | 2/2013 | Aranyi et al. |
| 8,551,091 B2 | 10/2013 | Couture et al. |
| 8,573,465 B2 | 11/2013 | Shelton, IV |
| 8,579,178 B2 | 11/2013 | Holsten et al. |
| 8,608,047 B2 | 12/2013 | Holsten et al. |
| 8,672,939 B2 | 3/2014 | Garrison |
| 8,783,541 B2 | 7/2014 | Shelton, IV et al. |
| 8,800,841 B2 | 8/2014 | Ellerhorst et al. |
| 8,858,547 B2 | 10/2014 | Brogna |
| 8,864,010 B2 | 10/2014 | Williams |
| 8,905,287 B2 | 12/2014 | Racenet et al. |
| 8,925,785 B2 | 1/2015 | Holsten et al. |
| 9,010,606 B2 | 4/2015 | Aranyi et al. |
| 9,055,961 B2 | 6/2015 | Manzo et al. |
| 9,192,378 B2 | 11/2015 | Aranyi et al. |
| 9,192,379 B2 | 11/2015 | Aranyi et al. |
| 9,211,120 B2 | 12/2015 | Scheib et al. |
| 9,216,019 B2 | 12/2015 | Schmid et al. |
| 9,345,479 B2 | 5/2016 | Racenet et al. |
| 9,717,497 B2 | 8/2017 | Zerkle et al. |
| 9,717,498 B2 | 8/2017 | Aranyi et al. |
| 9,936,949 B2 | 4/2018 | Measamer et al. |
| 10,111,659 B2 | 10/2018 | Racenet et al. |
| 10,130,367 B2 | 11/2018 | Cappola et al. |
| 10,231,732 B1 | 3/2019 | Racenet et al. |
| 10,285,693 B2 | 5/2019 | Kimsey et al. |
| 10,646,219 B2 | 5/2020 | Racenet et al. |
| 10,828,027 B2 | 11/2020 | Racenet et al. |
| 10,863,988 B2 | 12/2020 | Patel et al. |
| 11,234,700 B2 | 2/2022 | Ragosta et al. |
| 11,439,390 B2 | 9/2022 | Patel et al. |
| 11,504,124 B2 | 11/2022 | Patel et al. |
| 11,517,312 B2 | 12/2022 | Wixey |
| 2002/0165562 A1 | 11/2002 | Grant et al. |
| 2003/0135204 A1 | 7/2003 | Lee et al. |
| 2003/0181910 A1 | 9/2003 | Dycus et al. |
| 2004/0232199 A1 | 11/2004 | Shelton et al. |
| 2004/0267310 A1 | 12/2004 | Racenet et al. |
| 2005/0006430 A1 | 1/2005 | Wales |
| 2005/0006434 A1 | 1/2005 | Wales et al. |
| 2005/0070925 A1 | 3/2005 | Shelton, IV et al. |
| 2005/0070958 A1 | 3/2005 | Swayze et al. |
| 2005/0101991 A1 | 5/2005 | Ahlberg et al. |
| 2005/0113826 A1 | 5/2005 | Johnson et al. |
| 2005/0178813 A1 | 8/2005 | Swayze et al. |
| 2005/0187576 A1 | 8/2005 | Whitman et al. |
| 2005/0273084 A1 | 12/2005 | Hinman et al. |
| 2005/0273085 A1 | 12/2005 | Hinman et al. |
| 2006/0000868 A1 | 1/2006 | Shelton, IV et al. |
| 2006/0016853 A1 | 1/2006 | Racenet |
| 2006/0022014 A1 | 2/2006 | Shelton, IV et al. |
| 2006/0022015 A1 | 2/2006 | Shelton et al. |
| 2006/0024817 A1 | 2/2006 | Deguchi et al. |
| 2006/0025809 A1 | 2/2006 | Shelton, IV |
| 2006/0025810 A1 | 2/2006 | Shelton, IV |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0025816 A1 | 2/2006 | Shelton, IV |
| 2006/0049230 A1 | 3/2006 | Shelton, IV et al. |
| 2006/0097026 A1 | 5/2006 | Shelton, IV |
| 2006/0111209 A1 | 5/2006 | Hinman et al. |
| 2006/0111210 A1 | 5/2006 | Hinman |
| 2006/0161190 A1 | 7/2006 | Gadberry et al. |
| 2006/0190031 A1 | 8/2006 | Wales et al. |
| 2006/0226196 A1 | 10/2006 | Hueil et al. |
| 2007/0010838 A1 | 1/2007 | Shelton, IV et al. |
| 2007/0045379 A1 | 3/2007 | Shelton, IV |
| 2007/0250113 A1 | 10/2007 | Hegeman et al. |
| 2007/0262116 A1 | 11/2007 | Hueil et al. |
| 2008/0023522 A1 | 1/2008 | Olson et al. |
| 2008/0078804 A1 | 4/2008 | Shelton et al. |
| 2008/0086114 A1 | 4/2008 | Schmitz et al. |
| 2009/0277947 A1 | 11/2009 | Viola |
| 2010/0108740 A1 | 5/2010 | Pastorelli et al. |
| 2010/0145334 A1 | 6/2010 | Olson et al. |
| 2010/0179545 A1 | 7/2010 | Twomey et al. |
| 2010/0198248 A1 | 8/2010 | Vakharia |
| 2010/0331857 A1 | 12/2010 | Doyle et al. |
| 2011/0022078 A1 | 1/2011 | Hinman |
| 2011/0118707 A1 | 5/2011 | Burbank |
| 2011/0152879 A1 | 6/2011 | Williams |
| 2011/0174863 A1 | 7/2011 | Shelton, IV et al. |
| 2011/0251612 A1 | 10/2011 | Faller et al. |
| 2011/0251613 A1 | 10/2011 | Guerra et al. |
| 2011/0290851 A1 | 12/2011 | Shelton, IV |
| 2011/0290854 A1 | 12/2011 | Timm et al. |
| 2011/0295270 A1 | 12/2011 | Giordano et al. |
| 2011/0301603 A1 | 12/2011 | Kerr et al. |
| 2012/0000962 A1 | 1/2012 | Racenet et al. |
| 2012/0022584 A1 | 1/2012 | Donnigan et al. |
| 2012/0071891 A1* | 3/2012 | Itkowitz ............. G05B 15/02 715/863 |
| 2012/0223121 A1 | 9/2012 | Viola et al. |
| 2012/0228358 A1 | 9/2012 | Zemlok et al. |
| 2012/0248167 A1 | 10/2012 | Flanagan et al. |
| 2013/0015231 A1 | 1/2013 | Kostrzewski |
| 2013/0046303 A1 | 2/2013 | Evans et al. |
| 2013/0056521 A1 | 3/2013 | Swensgard |
| 2013/0068821 A1 | 3/2013 | Huitema et al. |
| 2013/0087599 A1 | 4/2013 | Krumanaker et al. |
| 2013/0098965 A1 | 4/2013 | Kostrzewski et al. |
| 2013/0126586 A1 | 5/2013 | Zhang et al. |
| 2013/0148577 A1 | 6/2013 | Terry et al. |
| 2013/0248577 A1 | 9/2013 | Leimbach et al. |
| 2013/0277410 A1 | 10/2013 | Fernandez et al. |
| 2013/0296922 A1 | 11/2013 | Allen, IV et al. |
| 2013/0327808 A1 | 12/2013 | Chen et al. |
| 2014/0001236 A1 | 1/2014 | Shelton, IV et al. |
| 2014/0005653 A1 | 1/2014 | Shelton, IV et al. |
| 2014/0021239 A1 | 1/2014 | Kostrzewski |
| 2014/0025071 A1 | 1/2014 | Sims et al. |
| 2014/0175152 A1 | 6/2014 | Hess et al. |
| 2014/0180286 A1 | 6/2014 | Marczyk et al. |
| 2014/0214049 A1 | 7/2014 | Jeong et al. |
| 2014/0257331 A1 | 9/2014 | Kim et al. |
| 2014/0263546 A1 | 9/2014 | Aranyi |
| 2014/0263550 A1 | 9/2014 | Aranyi et al. |
| 2014/0263559 A1 | 9/2014 | Williams et al. |
| 2014/0263567 A1 | 9/2014 | Williams et al. |
| 2014/0263569 A1 | 9/2014 | Williams et al. |
| 2014/0284372 A1 | 9/2014 | Kostrzewski |
| 2014/0343550 A1 | 11/2014 | Faller et al. |
| 2014/0343569 A1 | 11/2014 | Turner |
| 2014/0364851 A1 | 12/2014 | Batross et al. |
| 2015/0173789 A1 | 6/2015 | Baxter, III et al. |
| 2015/0209037 A1 | 7/2015 | Kostrzewski et al. |
| 2015/0250530 A1 | 9/2015 | Manzo et al. |
| 2015/0256609 A1* | 9/2015 | Morton ............. G06F 9/455 715/738 |
| 2015/0272575 A1 | 10/2015 | Leimbach et al. |
| 2015/0272576 A1 | 10/2015 | Cappola |
| 2015/0297227 A1 | 10/2015 | Huitema et al. |
| 2015/0297235 A1 | 10/2015 | Harris et al. |
| 2016/0038227 A1 | 2/2016 | Garrison |
| 2016/0120544 A1 | 5/2016 | Shelton, IV et al. |
| 2016/0157863 A1 | 6/2016 | Williams et al. |
| 2016/0174977 A1 | 6/2016 | Lytle, IV et al. |
| 2016/0175033 A1 | 6/2016 | Le |
| 2016/0192999 A1 | 7/2016 | Stulen et al. |
| 2016/0235489 A1* | 8/2016 | Gombert ............. A61B 34/37 |
| 2016/0270780 A1 | 9/2016 | Hall et al. |

(56) References Cited

U.S. PATENT DOCUMENTS

| | | |
|---|---|---|
| 2016/0287251 A1 | 10/2016 | Shelton, IV et al. |
| 2016/0338764 A1 | 11/2016 | Krastins et al. |
| 2017/0010578 A1 | 1/2017 | Miyakawa |
| 2017/0042604 A1 | 2/2017 | McFarland et al. |
| 2017/0079710 A1 | 3/2017 | Deville et al. |
| 2017/0097035 A1 | 4/2017 | Zimmerman et al. |
| 2017/0135746 A1 | 5/2017 | Tetzlaff et al. |
| 2017/0189028 A1 | 7/2017 | Aranyi |
| 2017/0231653 A1 | 8/2017 | Kapadia |
| 2017/0245857 A1 | 8/2017 | Shelton, IV et al. |
| 2017/0290584 A1 | 10/2017 | Jasemian et al. |
| 2017/0296172 A1 | 10/2017 | Harris et al. |
| 2018/0008265 A1 | 1/2018 | Hatanaka et al. |
| 2018/0021042 A1 | 1/2018 | Nicholas et al. |
| 2018/0161052 A1 | 6/2018 | Weir et al. |
| 2018/0168581 A1 | 6/2018 | Hunter et al. |
| 2018/0168622 A1 | 6/2018 | Shelton, IV et al. |
| 2018/0168628 A1 | 6/2018 | Hunter et al. |
| 2018/0168637 A1 | 6/2018 | Harris et al. |
| 2018/0168641 A1 | 6/2018 | Harris et al. |
| 2018/0168642 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0206844 A1 | 7/2018 | Harris et al. |
| 2018/0214200 A1 | 8/2018 | Nanditale et al. |
| 2018/0232951 A1* | 8/2018 | Alterovitz ............... A61B 34/30 |
| 2018/0296213 A1 | 10/2018 | Strobl |
| 2018/0310948 A1 | 11/2018 | Stamm et al. |
| 2018/0317915 A1 | 11/2018 | Mcdonald, II |
| 2019/0000454 A1 | 1/2019 | Swayze et al. |
| 2019/0015124 A1 | 1/2019 | Williams et al. |
| 2019/0099181 A1 | 4/2019 | Shelton, IV et al. |
| 2019/0125347 A1 | 5/2019 | Stokes et al. |
| 2019/0142531 A1 | 5/2019 | Wentworth et al. |
| 2019/0231350 A1 | 8/2019 | Scott et al. |
| 2019/0290374 A1* | 9/2019 | Ramadorai ............ A61B 34/37 |
| 2019/0298356 A1 | 10/2019 | Shelton, IV et al. |
| 2019/0314107 A1 | 10/2019 | Worrell et al. |
| 2019/0365458 A1 | 12/2019 | Whitlock et al. |
| 2020/0397430 A1 | 12/2020 | Patel et al. |
| 2021/0022736 A1 | 1/2021 | Wixey |
| 2021/0077101 A1 | 3/2021 | Patel et al. |
| 2021/0177495 A1 | 6/2021 | Ross et al. |
| 2021/0177500 A1 | 6/2021 | Khalaji |
| 2021/0212683 A1 | 7/2021 | Burbank |
| 2021/0267596 A1 | 9/2021 | Fanelli et al. |
| 2021/0386427 A1 | 12/2021 | Millman et al. |
| 2022/0015762 A1 | 1/2022 | Wixey et al. |
| 2022/0015763 A1 | 1/2022 | Wixey et al. |
| 2022/0015823 A1 | 1/2022 | Wilson et al. |
| 2022/0054130 A1 | 2/2022 | Overmyer et al. |
| 2022/0061836 A1 | 3/2022 | Parihar et al. |
| 2022/0061840 A1 | 3/2022 | Hites |
| 2022/0061841 A1 | 3/2022 | Wixey et al. |
| 2022/0071632 A1 | 3/2022 | Patel et al. |
| 2022/0079585 A1 | 3/2022 | Egan |
| 2022/0125428 A1 | 4/2022 | Ragosta et al. |
| 2022/0160358 A1 | 5/2022 | Wixey |
| 2022/0183686 A1 | 6/2022 | Wixey et al. |
| 2022/0192665 A1 | 6/2022 | Wellman |
| 2022/0346790 A1 | 11/2022 | Wellman |
| 2022/0378537 A1 | 12/2022 | Hites et al. |
| 2022/0395270 A1 | 12/2022 | Patel et al. |

FOREIGN PATENT DOCUMENTS

| | | |
|---|---|---|
| EP | 0641546 A1 | 3/1995 |
| EP | 1090592 A1 | 4/2001 |
| EP | 1728473 A1 | 12/2006 |
| EP | 1479346 B1 | 1/2007 |
| EP | 1621141 B1 | 7/2007 |
| EP | 1316290 B1 | 2/2012 |
| EP | 1754445 B1 | 10/2013 |
| EP | 3135225 A2 | 3/2017 |
| EP | 3158947 A1 | 4/2017 |
| EP | 3173029 A1 | 5/2017 |
| FR | 2828952 B1 | 12/2005 |
| JP | 5301166 B2 | 9/2013 |
| JP | 2014530653 A | 11/2014 |
| JP | 2016508792 A | 3/2016 |
| JP | 2016513570 A | 5/2016 |
| JP | 2017500146 A | 1/2017 |
| JP | 2017513564 A | 6/2017 |
| JP | 2017527396 A | 9/2017 |
| JP | 6411461 B2 | 10/2018 |
| JP | 2019141659 A | 8/2019 |
| SU | 405234 A1 | 9/1975 |
| SU | 886900 A1 | 12/1981 |
| SU | 1333319 A2 | 8/1987 |
| SU | 1442191 A1 | 12/1988 |
| SU | 1459659 A1 | 2/1989 |
| WO | WO-8602254 A1 | 4/1986 |
| WO | WO-9005489 A1 | 5/1990 |
| WO | WO-9734533 A1 | 9/1997 |
| WO | WO-03094743 A1 | 11/2003 |
| WO | WO-03094746 A1 | 11/2003 |
| WO | WO-03094747 A1 | 11/2003 |
| WO | WO-2012142872 A1 | 10/2012 |
| WO | WO-2014106275 A1 | 7/2014 |
| WO | WO-2017026141 A1 | 2/2017 |
| WO | WO-2017034803 A2 | 3/2017 |
| WO | WO-2017156070 A1 | 9/2017 |
| WO | WO-2017214243 A1 | 12/2017 |
| WO | WO-2018005750 A1 | 1/2018 |
| WO | WO-2018071497 A1 | 4/2018 |
| WO | WO-2018118402 A1 | 6/2018 |

OTHER PUBLICATIONS

International Preliminary Report on Patentability for Application No. PCT/US2019/017646, dated Aug. 27, 2020, 10 pages.

International Preliminary Report on Patentability for Application No. PCT/US2019/019501, dated Sep. 3, 2020, 7 pages.

International Search Report and Written Opinion for Application No. PCT/US2020/025655, dated Jul. 22, 2020, 8 pages.

International Search Report and Written Opinion for Application No. PCT/US19/17646, dated Apr. 16, 2019, 11 pages.

International Search Report and Written Opinion for Application No. PCT/US2019/019501, dated May 9, 2019, 8 pages.

International Search Report and Written Opinion for Application No. PCT/US2019/056979, dated Dec. 18, 2019, 8 pages.

International Search Report and Written Opinion for Application No. PCT/US2019/062344, dated Mar. 23, 2020, 17 pages.

International Search Report and Written Opinion for Application No. PCT/US2019/062768, dated Mar. 9, 2020, 15 pages.

International Search Report and Written Opinion for Application No. PCT/US2019/064861, dated Mar. 30, 2020, 18 pages.

International Search Report and Written Opinion for Application No. PCT/US2019/066513, dated Apr. 21, 2020, 8 pages.

International Search Report and Written Opinion for Application No. PCT/US2019/066530, dated Apr. 21, 2020, 8 pages.

International Search Report and Written Opinion for Application No. PCT/US2020/020672, dated Jun. 29, 2020, 10 pages.

International Search Report and Written Opinion for Application No. PCT/US2020/033481, dated Sep. 3, 2020, 22 pages.

European Search Report (Corrected version) for Application No. EP19750317.0, dated Mar. 28, 2022, 26 pages.

Partial European Search Report for Application No. EP19757451.0, dated Feb. 2, 2022, 12 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

International Search Report and Written Opinion for Application No. PCT/US2021/012284, dated May 6, 2021, 23 pages.

Supplementary European Search Report for Application No. EP19873128.3, dated Jun. 22, 2022, 7 pages.

* cited by examiner

REMOTELY CONTROLLING A SYSTEM USING VIDEO

CROSS-REFERENCES TO RELATED APPLICATIONS

This application claims priority to U.S. Provisional Patent Application No. 62/869,587, filed Jul. 2, 2019, the content of which is incorporated herein in its entirety.

FIELD

The present disclosure generally relates to remote control systems and, more particularly, relates to the remote control of a system using teleoperation.

BACKGROUND

One of the more significant medical advancements in recent decades has been in the field of surgical robotics technologies. For example, robotic surgical systems now allow surgeons teleoperative abilities to control surgical instruments with improved precision and range of motion, while also providing enhanced visualization and access to hard-to-reach areas. These systems have been able to provide patients with a minimally invasive alternative to open and laparoscopic surgeries. One such system is the da Vinci™ Surgical System, by Intuitive Surgical, Inc. of Sunnyvale, Calif. The da Vinci™ Surgical System is a robotically controlled surgical system that provides a surgeon console or control center and a patient-side cart. The patient-side cart has multiple movable arms for mechanically controlling attached surgical instruments. A drive system with a mechanical interface enables the surgeon to remotely move and position respective instruments with precision during medical procedures, while seated in the ergonomically designed console. A high-definition camera allows the surgeon a highly magnified, high-resolution 3D image of the surgical site once the camera is placed inside the patient. Coupled with the use of controllers on the surgeon console, the surgeon can translate his own hand movements into smaller, precise movements of tiny surgical instruments in the patient.

Current robotic surgical systems typically lack the functionality to interoperate with recently developed portable systems, such as mobile phones, tablet computers, and the like. The availability, power, and flexibility of such systems offer surgeons the opportunity to access information that can improve their ability to assess a patient's condition during the surgery and, thereby, provide improved results. However, modifying an existing system to accommodate these new devices typically involves significant modification the existing system's hardware, firmware, and software. It would therefore be desirable to enable recently developed systems to interoperate with existing systems, without making significant modifications to the existing systems.

BRIEF SUMMARY

The present disclosure is generally directed to performing remote control of a system using another system. A system in accordance with the present disclosure performs operations including detecting a video signal of an auxiliary system at a video input, wherein the video signal including images encoded with control information. The operations also include determining that the images included in the video signal include the control information. The operations further include extracting the control information from the images. Additionally, the operations include modifying operations of the system based on the control information.

In some implementations, an auxiliary system generates a video signal displayed by a primary system. The auxiliary system can embed control information within image data transmitted in the video signal to control modes of operation of the primary system. The control information may be embedded via steganography techniques from the mobile device. In some implementations, when the auxiliary system is communicating with the primary system, the primary system may adjust its display and user interface. In some implementations, the primary system may disable predetermined functions (e.g., teleoperations) when a user is using the auxiliary system to control the primary system. Some implementations may implement certain data security and integrity features, such as checksums or error-correcting codes. Some implementations may also employ cryptographic features for authentication and authorization.

In one exemplary implementation, the primary system can be a robotic surgical system and the auxiliary system can be a mobile device. A user of the mobile device may interact with the robotic surgical system and control information to indicate a desired state of operation for the robotic surgical system via a video signal, wherein the video signal comprises first data representing an image or video captured by the mobile device and second data representing the control information. The mobile device may selectively change the first data based on the control information and transmit the video signal to the robotic surgical system. The robot surgical system may decode the control information from the video signal and modify a mode of operation of the console based on the control information. For example, based on the control information, the surgical system performs operations such as, changing a location of a display, present a user interface, and selectively enable and disable the at least one robotic arm.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several implementations of the disclosure and together with the description, explain the principles of the disclosure.

DETAILED DESCRIPTION

The present disclosure provides systems and methods for an auxiliary system to remotely control behaviors of a primary system. In some implementations, the auxiliary system can be a mobile device, the primary system can be a robotic surgical system, and the video signal can include images transmitted from a video source of the mobile device for display by the robotic surgical system. In accordance with aspects of the present disclosure, the auxiliary system may incorporate the control information into data comprising the images transmitted to the primary system. For example, the auxiliary system can embed the control information in the image data using steganography techniques. In some implementations, the control information provided by the auxiliary system controls the primary system to modify a behavior, an operation, or an output of a user interface of the primary system. For example, the surgical system may change display modes and suspend teleoperation of surgical instruments in response to receiving the control information included in video images from the mobile device. Further, some implementations may authenticate the identity and the integrity of the auxiliary system, the video connection, and the video signal. For example, the primary system and the auxiliary system may use cryptographic techniques, such as digital signatures or one-time passwords.

As disclosed herein, implementations disclosed herein enable auxiliary systems to interoperate and control an existing primary system without significant modification of the primary system. For example, the existing surgical system may have hardware, firmware, and/or software that are incompatible with a newly or recently developed mobile device. Consequently, the surgical system may be unable to interoperate with the mobile device. However, in accordance with aspects of the present disclosure, the auxiliary system can transparently embed control information (e.g., application data) in image data using steganography techniques and transmit them to an existing video input (e.g., Digital Video Interface ("DVI"), high-definition serial digital interface ("HD-SDI"), and high-definition multimedia interface ("HDMI")) of the primary system in a video signal. The primary system can detect the video signal, extract the control information from the image data contained therein, and modify its operation based on extracted control information.

Figure 1:
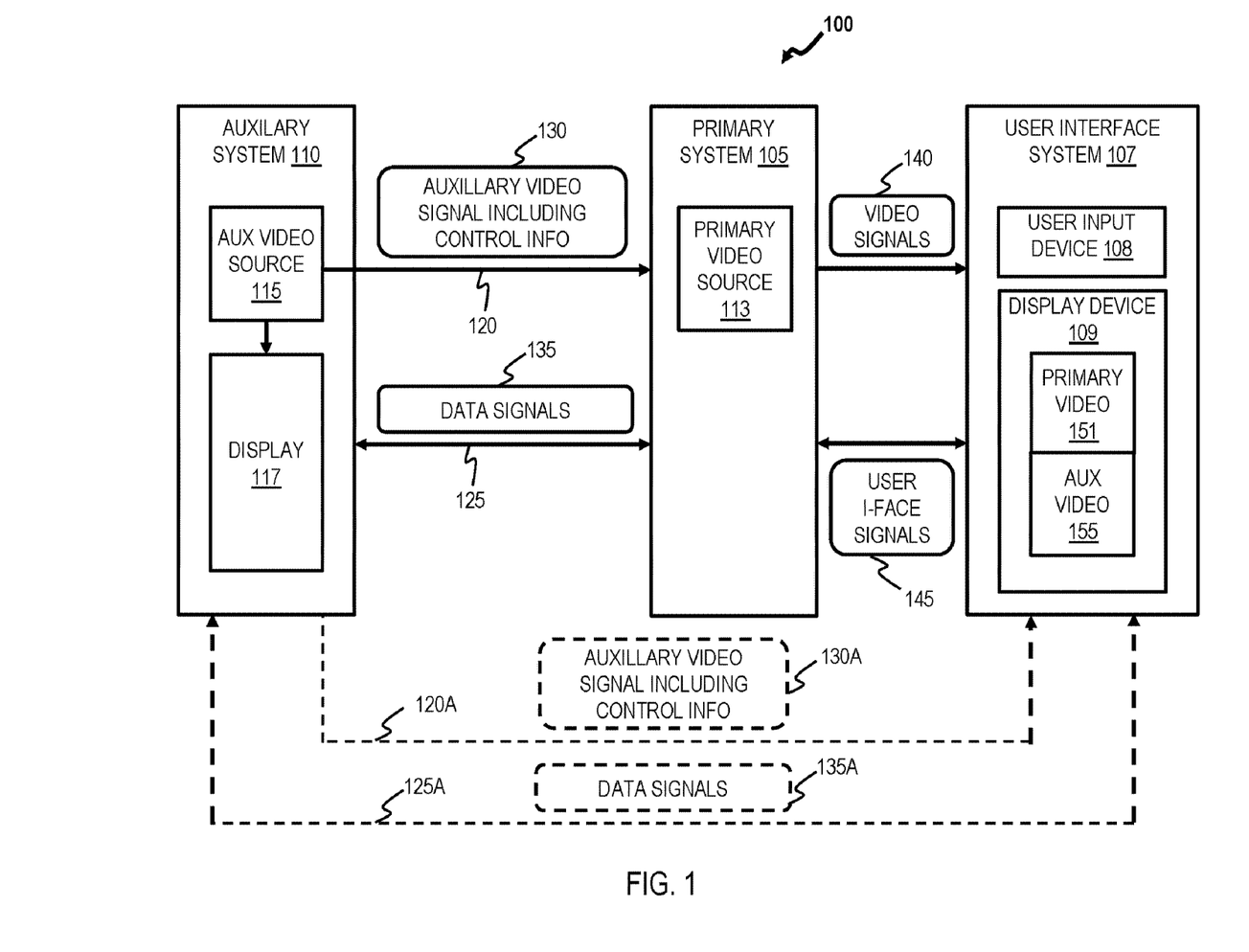
FIG. 1 shows a block diagram illustrating an example of an environment for implementing systems and processes in accordance with aspects of the present disclosure.

FIG. 1 shows a functional block diagram illustrating an example of an environment 100 for implementing systems and processes in accordance with aspects of the present disclosure. The environment can include a primary system 105, a user interface system 107, and an auxiliary system 110. In some implementations, the environment 100 can be a surgical system, wherein the primary system 105 and the user interface system 107 are a patient-side cart and a surgeon console, respectively. For example, the patient-side cart, the surgeon console, and the electronics/control can be the same or similar to those provided in the da Vinci® Xi (model no. IS4000) commercialized by Intuitive Surgical, Inc. of Sunnyvale, Calif., as previously described herein. In some such implementations, the primary system 105 can include tools to perform minimally invasive robotic surgery by interfacing with and controlling a variety of surgical instruments. For example, the primary system 105 can include one or more user-controllable arms configured to hold, position, and manipulate various surgical instruments and other tools.

The user interface system 107 can receive (directly or indirectly) video signals 140 and user interface signals 145 from the primary system 105 and the auxiliary system 110. While FIG. 1 illustrates the user interface system 107 being directly connected to the primary system 105 and indirectly connected to the auxiliary system 110, it is understood that other implementations of the environment 100 can rearrange the primary system 105, the user interface system 107, the auxiliary system 110, and the connections therebetween. For example, as indicated by the dashed lines in FIG. 1, some implementations of the environment 100 can connect auxiliary system 110 directly to the user interface system 107. Also, some implementations can combine some or all of the hardware and functionality of the user interface system 107 with the primary system 105.

In some implementations, the user interface system 107 can include one or more user-input devices 108 for operating the primary system 105. The input device 108 can include, for example, joysticks, computer mice, computer trackballs, foot pedals, touchscreen displays, or other suitable input devices. Additionally, the user interface system 107 can include one or more display devices 109 for displaying still images and video. The display device 109 can be, for example, a cathode ray tube (CRT) display, a liquid crystal display (LCD), a light-emitting diode (LED) display, a stereoscopic display, or other suitable display technology.

Figure 5:
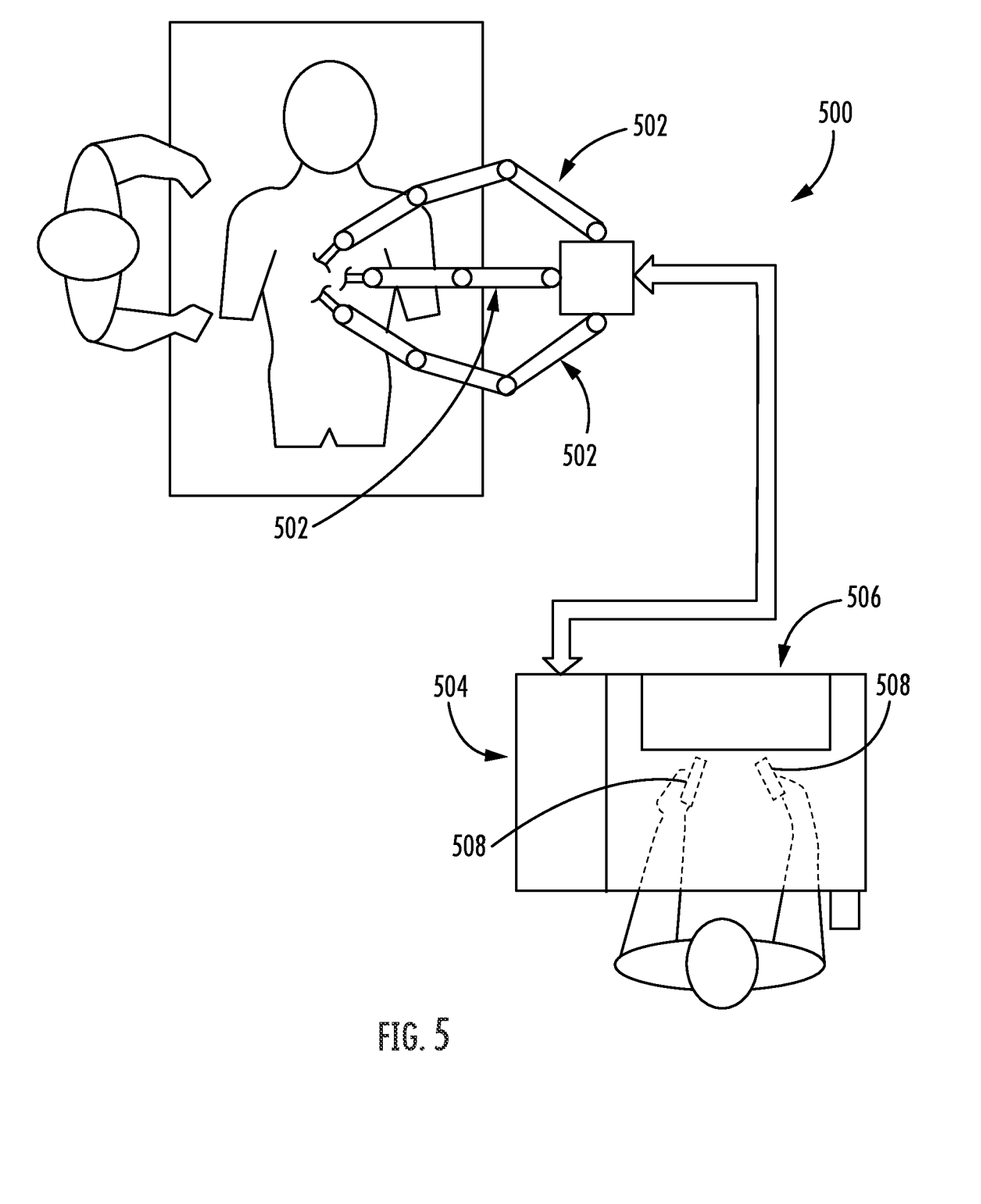
FIG. 5 illustrates a robotic surgical system in accordance with aspects of the present disclosure.

In some implementations, the user interface system 107 can be a surgeon console for operating a robotic surgical system 500 (see FIG. 5). Robotic surgical system 500 may include a console 504 having a three-dimensional (3D) display 506 and one or more controls 508 for controlling the instruments 502. Through the input devices, the user interface system 107 serves as a controller by which the instruments 502 (such as one or more robotic arms) mounted at the robotic surgical system 500 act as an implement to achieve desired motions of the surgical instrument(s), and accordingly perform a desired surgical procedure. It is understood, however, that the environment 100 is not limited to receiving inputs at the user interface system, and inputs may be received at any device which can be configured to realize a manipulation of the surgical instrument(s) at the primary system 105. For example, a surgical instrument at the primary system 105 may be manipulated at the primary system 105 through user interface system 107 in combination with another surgical instrument support device, or entirely through the other surgical support device.

Additionally, the user interface system 107 can receive image data from the primary system 105 and the auxiliary system 110, and can present such images using the display device 109. For example, the user interface system 107 can receive video signals 140 including image data from a primary video source 113 of the primary system and image data from an auxiliary video source 115 of the auxiliary system 110. The user interface system 107 can display the received images together on the display device 109. For example, the primary video source 113 can be an endoscopic camera that outputs primary video 151 that can be displayed to a surgeon using the display device 109 of the user interface system 107. Further, the auxiliary video source 115 can output auxiliary video 155 that can be displayed together with the primary video 151 on the display device 109. In some implementations, the user interface system 107 can present the primary video 151 and the auxiliary 155 as separate tiles in non-overlapping areas of the display device 109. It is understood that, in some implementations, the primary system 105 or the user interface system 107 can combine the primary video 151 and the auxiliary video 155. For example, the primary video 151 and the auxiliary video 155 can be indexed and/or overlaid to provide a single mixed image on the display device 109.

The auxiliary system 110 can be a computing system including a graphic user interface that displays images from an auxiliary video source 115. In some implementations, the auxiliary system 110 is a mobile personal computing device. For example, the auxiliary system 110 can be a laptop computer, a tablet computer, a smart phone, a video camera, or other such device. The auxiliary system 110 can be connected to the primary system 105 and the user interface system 107 by a video channel 120 and a data channel 125. In some implementations, the auxiliary video source 115 can be an image sensor of the auxiliary system 110. For example, the auxiliary video source 115 can be video captured by a camera of the auxiliary system 110 and presented on a display 117 of the auxiliary system 110. Additionally, in some implementations, the auxiliary video source 115 can be image data stored locally by the axillary system 110, or image data accessed by the auxiliary system 110 at a remote repository. Additionally, the auxiliary video source 115 can be images stored locally by the auxiliary system 110, or retrieved (e.g., accessed or streamed) from a remote system over a communication link or network (e.g., the Internet).

The video channel 120 can include one or more communication links, which can be any combination of wired and/or wireless links using any combination of video transmission techniques and video protocols. In some implementations, the video channel 120 may be a wired video link (e.g., S-video, HDMI, DVI, DisplayPort, or other suitable video connection). In other implementations, the video channel 120 can be a wireless video link (e.g., wireless home digital interface ("WHDI"), WirelessHD™, WiGig™, AirPlay™, Miracast™, WiDi™, or another suitable wireless video connection). Further, in some implementations, the video channel 120 can be a unidirectional video connection configured solely to transmit video signals or audiovisual signals. For example, the unidirectional video connection can be configured to solely function at particular video transmission frequencies and solely using video transmission protocols.

The information channel 125 can include one or more communication links or data links. The information channel 125 can comprise any combination of wired and/or wireless links; any combination of one or more types of networks (e.g., the Internet, a wide area network, a local area network, a virtual private network, etc.); and/or utilize any combination of transmission techniques and protocols and/or a communication networks, such as a local area network, a wide area network, or the Internet. In some implementations, the information channel can include, for example, a universal serial bus ("USB"), FireWire, Wi-Fi, Bluetooth, Ethernet, or other suitable data communication links. In some implementations, the auxiliary system 110 solely uses the information channel 125 to transmit non-video data signals 135, while solely using the video channel 120 for transmitting video or audiovisual signals 130. Some implementations lack information channels 125 and 125A, and the auxiliary system 110 solely uses the video channel 120 to communicate with the primary system 105 using the auxiliary video signal 130.

In a non-limiting example of an implementation consistent with the present disclosure, the primary system 105 can be a surgical system, and the auxiliary system 110 can be a mobile device connected to the surgical system solely by the video channel 120. For example, a user can connect the mobile device to the surgical system 100 by connecting a video transmission cable (e.g., HDMI) as the video channel 120 to a video input connector of the primary system 105 or the user interface 107. In accordance with aspects of the present disclosure, the user of the auxiliary system 110 can provide control inputs that change the behavior or state of the primary system 105 using the auxiliary system 110. The control inputs can modify behaviors, operations, and outputs of the primary system 105. For example, where the primary system is a robotic surgical system, the control information from the mobile device may cause the surgical system to change display modes. The display modes may include an interface for controlling system modes, such as: following mode (follower surgical instruments follow movements of the primary tool grips), clutch mode (disengaging follower actuation from primary movement), camera control mode (enabling endoscope movement), energy tools mode (enabling surgical energy tool control (e.g., electrocautery tools), camera focus mode (enabling camera focus control), arm swapping (allowing various primary and follower arm control combinations), and tiled auxiliary image swapping mode (also referred to as "tilepro") for enabling control of various picture displays in the surgeon's display, e.g., swapping between a full screen display and a display in which the surgeon views two or more separate images or data screens.

The auxiliary system 110 can convert the user's control inputs to control information, incorporate the control information into video images, and transmit the video images to the primary system 105 in the video signal 130 via the video channel 120. In the implementations, the auxiliary system 110 uses steganographic techniques to incorporate the control information within the video images (see the optional step at block 401 in FIG. 4). For example, in one implementation, the auxiliary device 110 may vary pixels at the edge of the image, or make subtle adjustments to color values of the image data (e.g., by modifying the least significant bits). By doing so, the auxiliary system 110 can minimize alterations to the video images to render image data incorporating control inputs of a user.

Further, the primary system 105 can receive the transmission of the auxiliary video signal 130 including the control information, interpret the video images to extract the control information, and modify its behavior, operation, or output of the surgical system based on the control information.

Figure 2:
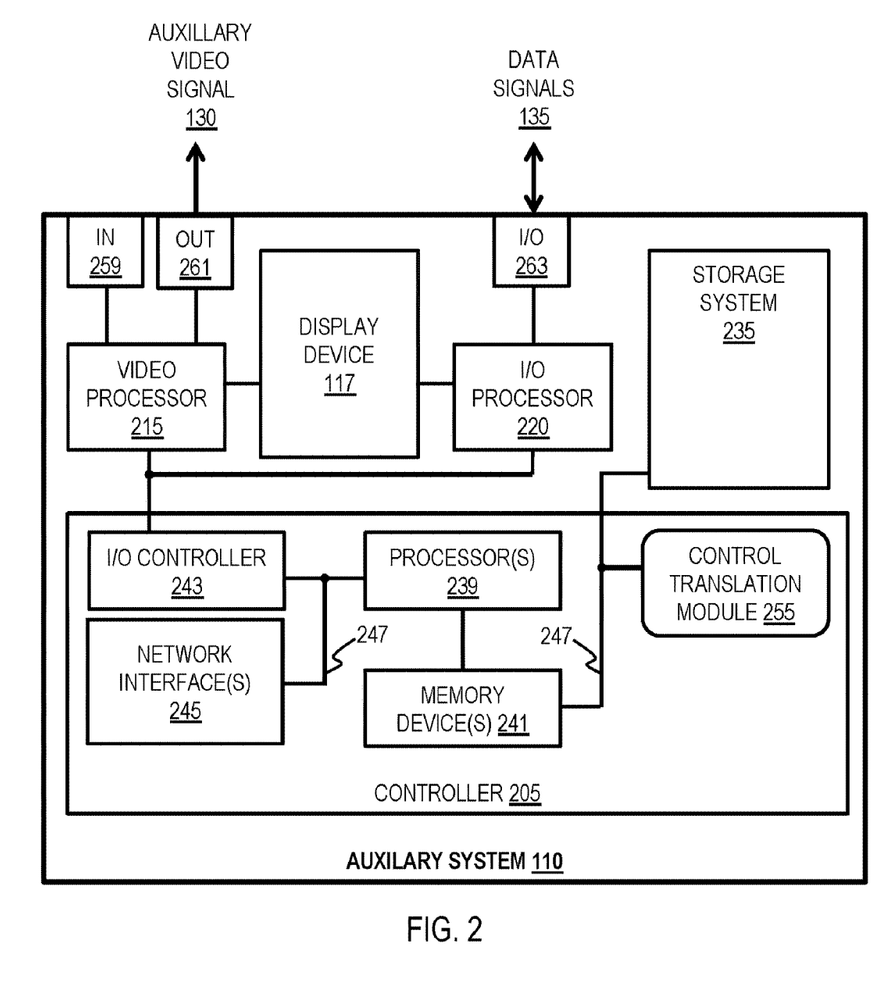
FIG. 2 shows a block diagram illustrating an auxiliary system in accordance with an implementation of the disclosure.

FIG. 2 shows a block diagram illustrating an auxiliary system 110 in accordance with an implementation of the disclosure. The auxiliary system 110 can include a controller 205, a video processor 215, input/output (I/O) processor 220, a display 117, and a storage system 235. In some implementations, the controller 205 can include a processor 239, memory devices 241, an I/O controller 243, a network interface 245, and a bus 247. The memory devices 241 can include a read-only memory (ROM), a random-access memory (RAM)(e.g., static RAM), and an operating system (O/S). The controller 205 can be in communication with the video processor 215, the I/O processor 220 and the storage system 235. The bus 116 can provide a communication link between the components in the controller 205.

In general, processor 239 executes computer program instructions, which can be stored in the memory devices 241 and/or the storage system 235. In accordance with aspects of the present disclosure, the program instructions can include a control translation module 255 that, when executed by the processor 220, perform one or more of the functions described herein. It is understood that the control translation module 255 can be implemented as one or more sets of program code stored in memory 241 as separate or combined modules.

While executing the computer program instructions, the processor 239 can read and/or write data to/from memory 241, storage system 235, and the control translation module 255. The program code executes the processes of the present disclosure, for example, by modifying video image data to incorporate control information. In some implementations of the present disclosure, control translation module 255 is computer program code stored in, for example, the memory device 241 or the storage system 235 that, when executed by the processor 239, causes controller 205 to performs steganographic encoding of video images. For example, the control information can be application data embedded in a video image based on ancillary data, metadata substitution, least significant bit substitution or adaptive substitution, or frequency space manipulation of data in a carrier, i.e., the original image or video signal generated by an auxiliary device. The control translation module 255 can use existing steganographic tools, such as Xiao Steganography, Image Steganography, Steghide, Crypture, Rsteg, Ssuite Piscel, OpenStego, and SteganPeg, that encode and decode information into and from images. In some implementations, control translation module 255 employs steganographic techniques to adjust pixel values (color, brightness, etc.), such as the least significant bits or metadata within a portion or across all of its display to encode application data 225, such as control information messages, user interface inputs, etc. within the image or video signal.

The video processor 215 can include an input connection 259 and output connection 261. In some implementations, the input connection 259 is solely a video input solely configured to receive video signals or audiovisual signals. Likewise, in some implementations, the output connection 261 is solely a video output solely configured to transmit video signals or audiovisual signals. The video processor 215 can process image data received from the controller 205 to drive the display 117 and to generate the auxiliary video signal 130. In accordance with aspects of the present disclosure, the image data from the controller can include control information incorporated the control translation module 255.

The I/O processor can include an input/output connection 263. In some implementations, the input connection 259 is solely a data input solely configured to receive data signals. The I/O processor 220 can process data received from the controller 205 and convert it to a data signal for transmission via the I/O connector 263. The I/O processor 220 can also process data signals received from the I/O connection 263, convert it to a data, and provide the data to the controller 205. Further, the I/O processor can exchange information with the display 117. For example, the I/O can process user inputs generated by a touch screen display.

Figure 3:
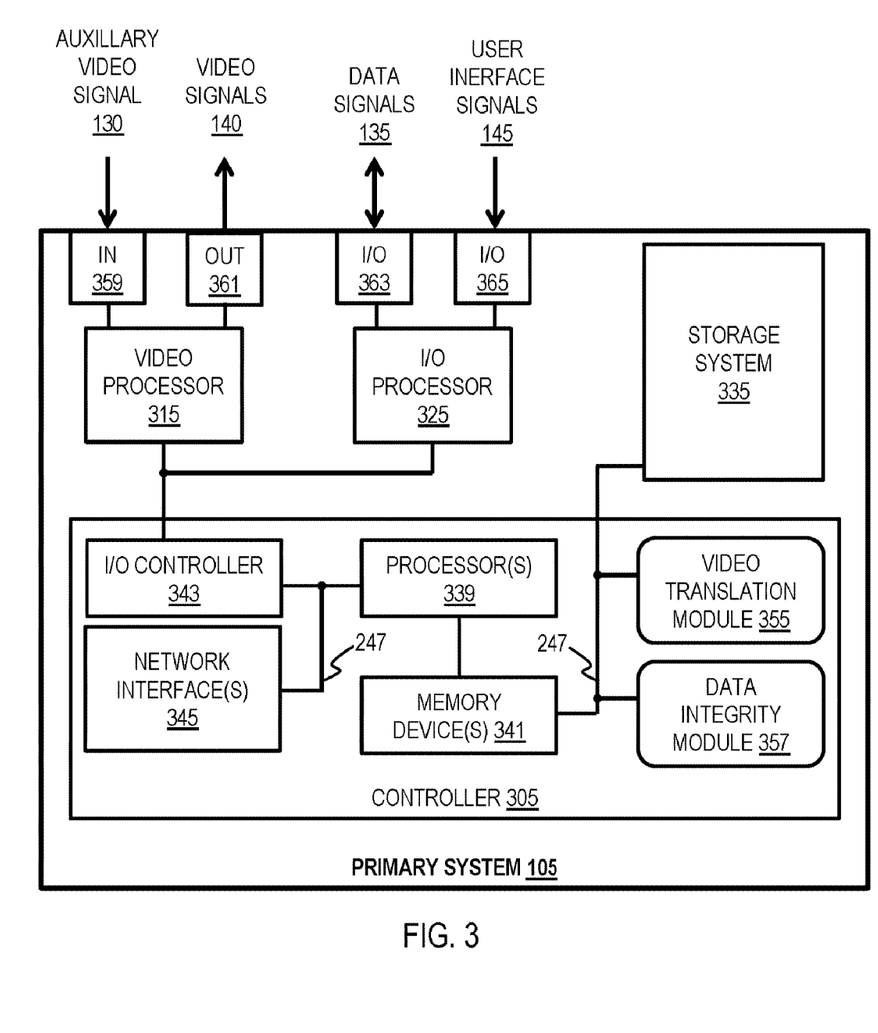
FIG. 3 shows a block diagram illustrating a primary system in accordance with an implementation of the disclosure.

FIG. 3 shows a block diagram illustrating a primary system 105 in accordance with some implementations of the disclosure. The primary system 105 can include a controller 305, a video processor 315, an input/output (I/O) processor 325, a storage system 335, a processor 339, memory devices 341, an I/O controller 343, a network interface 345, and a bus 247, all of which can be the same or similar to that previously described herein.

In accordance with aspects of the present disclosure, the program instructions can include a video translation module 355 and a data integrity module 357 that, when executed by the processor 339, perform one or more of the functions described herein. In some implementations, the video translation module 355 can be the same or similar to the control translation module 255 described above regarding FIG. 2. It is understood that video translation module 355 and the data integrity module 357 can be implemented as one or more sets of program code stored in memory 341 as separate or combined modules.

As will be described further below, in some implementations, the video translation module 355 detects a video signal, such as the auxillary video signal 130 received by the primary system 105, and determine whether it contains video data including control information. If so, the video translation module 355 can modify the operation of the primary system 105 (including the user interface system 107). The primary system 105 may react to control information by, for example, adjusting its own behavior, mode, or outputs. In some implementations, the control information changes modes of the primary system to enable/disable teleoperation of the primary system 105 (see the optional step at block 413B in FIG. 4).

The data integrity module 357 can ensure integrity of information received in the auxiliary video signal 130 to prevent unexpected system behavior of the primary system 105. In some implementations, the data integrity module 357 performs various data integrity checks, such as checksums, error-correcting code, or other suitable verification techniques, for example, based on data embedded in the control information of the auxiliary video signal 130. In one implementation, data integrity module 357 may perform cryptographic functions to verify the identity, authenticity, and authority the source of the auxiliary video signal (e.g., auxiliary system 110) before the control information is permitted to trigger behavior changes by primary system 105. For example, in one implementation, the primary system 105 may employ a varying access code such as those used in two-factor authentication (e.g., a hash function that generates a constantly-varying one-time-password from a shared secret).

Figure 4:
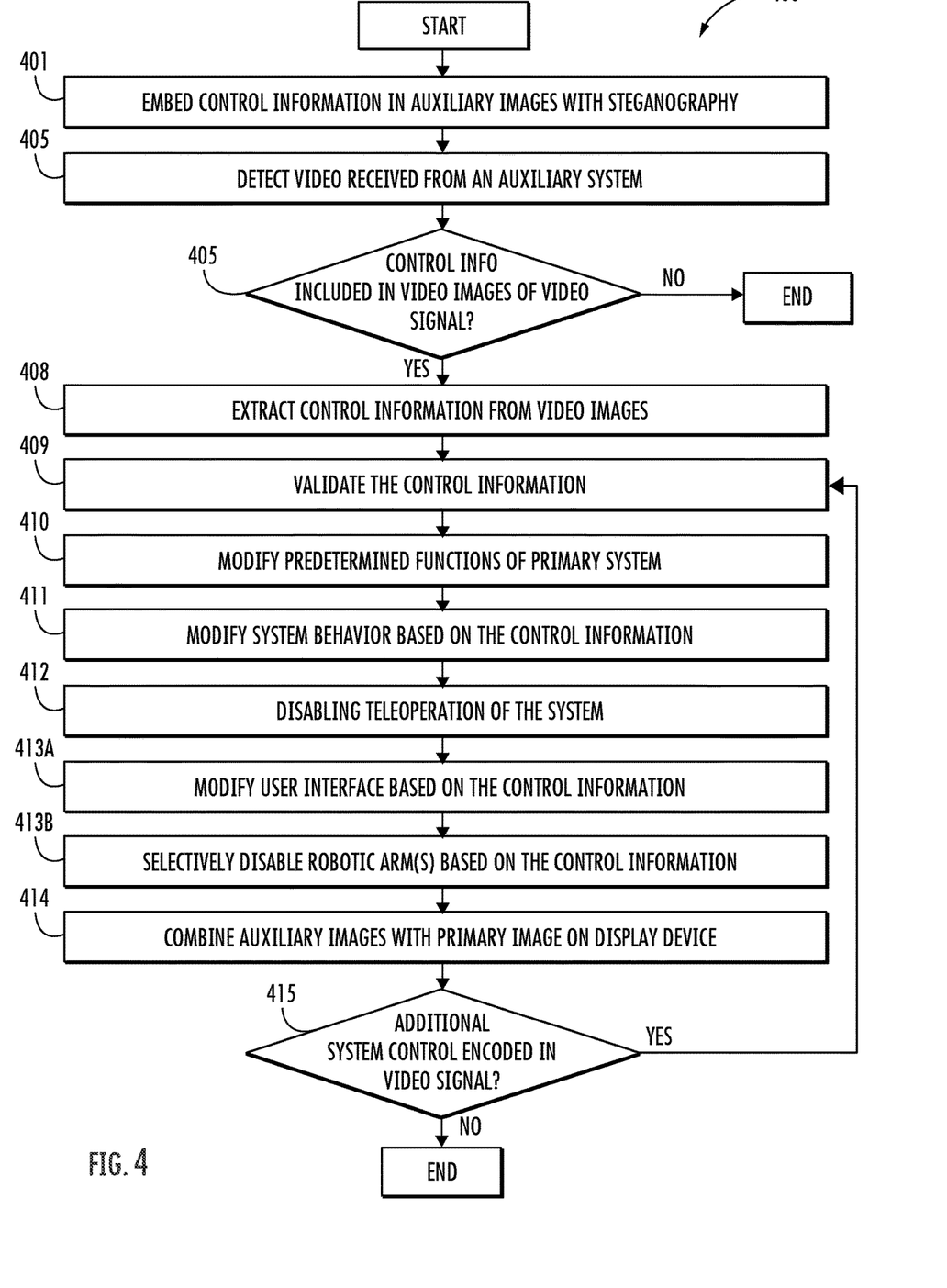
FIG. 4 shows a process flow diagram illustrating an example method of operating the gaming system in accordance with aspects of the present disclosure.

The flow block diagram in FIG. 4 illustrates an example of the functionality and operation of possible implementations of systems, methods, and computer program products according to various implementations consistent with the present disclosure. Each block in the flow diagram of FIG. 4 can represent a module, segment, or portion of program instructions, which includes one or more computer executable instructions for implementing the illustrated functions and operations. In some alternative implementations, the functions and/or operations illustrated in a particular block of the flow diagram can occur out of the order shown in FIG. 4. For example, two blocks shown in succession can be executed substantially concurrently, or the blocks can sometimes be executed in the reverse order, depending upon the functionality involved. Further, in some implementations, the flow diagram can include fewer blocks or additional blocks. It will also be noted that each block of the flow diagram and combinations of blocks in the diagram can be implemented by special purpose hardware-based systems that perform the specified functions or acts, or combinations of special purpose hardware and computer instructions.

FIG. 4 shows a flow block diagram illustrating an example of a process 400 for controlling modes, behaviors, and states of a system (e.g., primary system 105) using control information incorporated into images transmitted in a video signal from an auxiliary system (e.g., auxiliary system 110). Turning to block 405 in FIG. 4, the system detects video (e.g., auxiliary video signal 130 or 130A) received from the auxiliary system. In some implementations, the system may detect a physical connection of a cable to a video connection (e.g. video input 359). In other implementations, the system can detect a wireless signal received by the video connection. Additionally, in some implementations, the system may respond to detection of the video at block 405 by providing an indication at the primary system or at a user interface (e.g., user interface system 107). For example, the system may display the received video (e.g., auxiliary video 155) on a display device (e.g., display device 109). The system may also provide an alert of the received video using, for example, an audiovisual indication or a pop-up message on the display.

At block 407, the system (e.g., executing video translation module 355) determines whether the video signal received at block 405 includes images including control information. If the video images do not include image data having control information (e.g., block 407 is "No,") the method 400 ends. On the other hand, if the system determines that the video signal includes image data having control information (e.g., block 407 is "Yes,") then at block 408 the system extracts the control information from the video images received in the video signal. For example, as described above, the system can use steganographic tools to detect and extract control information from the video signal received at block 405. At block 409, the system can validate the information received from the auxiliary system at block 405. In some implementations, the system validates the control information extracted at block 408. In some implementations, the system can validate information provided in the video signal received at block 405 prior to the extraction at block 408. The validation at block 409 can verify that the information received from the auxiliary system is authentic and that it represents actual control information. As previously described herein, validation of the information may utilize cryptographic techniques, such as digital signatures or one-time passwords. Additionally, the validation can use techniques such as cyclic redundancy check ("CRC") or checksums.

At block 410, the system can modify one or more predetermined functions based on the control information extracted at block 408. In some implementations, after validating the control information at block 409, the system can limit the functionality of the primary system or the user interface system to prevent erroneous or malicious control information from causing the primary system to perform undesirable operations. For example, modifying the predetermined functions can include suspending teleoperation of the primary system by the user interface system while receiving valid control information from the auxiliary system. Additionally, in some implementations, modifying the predetermined functions can include disabling a data input/output interface (e.g., I/O 263 and I/O processor 220) while receiving valid control information from the auxiliary system (see the optional step at block 412).

At block 411 and the optional step at block 413A, the system can modify its behaviors, operations, and outputs based on the control information extracted at block 409. For example, as shown in the optional step at block 414, the system may combine video generated at the system (e.g., primary video 151 from primary video source 113) with video received from the auxiliary system (e.g., auxiliary video 155 of auxiliary video source 115) to display a tiled image on a user interface (e.g., display device 109 of user interface system 107). In a particular example, the system may generate a tiled display mode (e.g., a "TilePro Mode" of the da Vinci™ Surgical System) including an arrangement of two auxiliary video inputs (picture archiving and communication system ("PACS"), ultrasound, room camera, etc.) along with the operative image in main display portion. Additionally, in some implementations, the control information received in the auxiliary video signal may control a size and scaling of the display. For example, when two auxiliary inputs are present, the 3D image provided by the stereoscopic display on auxiliary system 110 may be scaled on the screen.

At block 415, the system determines whether the video signal received at block 405 includes additional control information. If the video images do not include additional control information (e.g., block 415 is "No,") the method 400 ends. On the other hand, if the system determines that the video signal includes image data having additional control information (e.g., block 415 is "Yes,") then the process 400 iteratively returns to block 409 and continues as described above.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is also to be understood that the terminology used herein is for the purpose of describing examples of implementations and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B." In addition, where features or aspects of the disclosure are described in terms of Markush groups, those skilled in the art will recognize that the disclosure is also thereby described in terms of any individual member or subgroup of members of the Markush group.

What is claimed is:

1. A robotic surgical system comprising:
    a display device;
    an endoscopic camera configured to generate a primary image on the display device;
    at least one robotic arm configured to perform surgical maneuvers on a patient;
    a console having a three-dimensional (3D) display and one or more controls for controlling the at least one robotic arm;
    a video input;
    a processor; and
    a computer-readable data storage device storing program instructions that, when executed by the processor, control the robotic surgical system to:
    detect a video signal of an auxiliary system at the video input, the video signal including one or more auxiliary images encoded with control information for the robotic surgical system;
    determine that the one or more auxiliary images included in the video signal include the control information;
    extract the control information from the one or more auxiliary images;
    selectively disabling the at least one robotic arm based on the control information; and
    combine the one or more auxiliary images with the primary image on the display device.

2. The robotic surgical system of claim 1, wherein the control information controls a behavior of the robotic surgical system.

3. The robotic surgical system of claim 1, wherein the control information modifies a user interface of the robotic surgical system.

4. The robotic surgical system of claim 1, wherein the video input comprises a unidirectional video input configured to solely receive video signals or audiovisual signals.

5. The robotic surgical system of claim 1, wherein the control information is solely transmitted within the one or more auxiliary images.

6. The robotic surgical system of claim 1, wherein the control information is embedded in the one or more auxiliary images using steganography.

7. The robotic surgical system of claim 1, wherein the program instructions further control the robotic surgical system to modify a predetermined function of the robotic surgical system in response to detecting the video signal.

8. The robotic surgical system of claim 7, wherein modifying the predetermined function comprises disabling teleoperation of the robotic surgical system.

9. A method of remotely controlling a robotic surgical system including at least one robotic arm configured to perform surgical maneuvers on a patient and a console having a three-dimensional (3D) display and one or more controls for controlling the at least one robotic arm, the method comprising:
    generating a primary image from an endoscopic camera onto a display device;
    detecting, by a processor, a video signal of an auxiliary system at a video input, the video signal including one or more auxiliary images encoded with control information;
    determining, by the processor, that one or more auxiliary images included in the video signal include the control information;
    extracting, by the processor, the control information from the one or more auxiliary images;
    selectively disabling, by the processor, the at least one robotic arm based on the control information; and
    combining the one or more auxiliary images with the primary image on the display device.

10. The method of claim 9, wherein the control information controls a behavior of the robotic surgical system.

11. The method of claim 9, wherein the control information modifies a user interface of the robotic surgical system.

12. The method of claim 9, wherein the video input comprises a unidirectional video input configured to solely receive video signals or audiovisual signals.

13. The method of claim 9, wherein the control information is solely transmitted within the one or more auxiliary images.

14. The method of claim 9, wherein the control information is embedded in the one or more auxiliary images using steganography.

15. The method of claim 9, further comprising modifying a predetermined function of the robotic surgical system in response to detecting the video signal.

16. The method of claim 15, wherein modifying the predetermined function comprises disabling teleoperation of the robotic surgical system.

* * * * *